(12) United States Patent
Metcalfe et al.

(10) Patent No.: US 6,618,155 B2
(45) Date of Patent: Sep. 9, 2003

(54) METHOD AND APPARATUS FOR SCANNING LUMBER AND OTHER OBJECTS

(75) Inventors: Leonard Metcalfe, Delta (CA); Barry Dashner, Delta (CA)

(73) Assignee: LMI Technologies Inc., Delta (CA)

( * ) Notice: Subject to any disclaimer, the term of this patent is extended or adjusted under 35 U.S.C. 154(b) by 0 days.

(21) Appl. No.: 09/931,178

(22) Filed: Aug. 17, 2001

(65) Prior Publication Data

US 2002/0024677 A1 Feb. 28, 2002

Related U.S. Application Data (60) Provisional application No. 60/227,015, filed on Aug. 23, 2000, and provisional application No. 60/227,017, filed on Aug. 23, 2000.

(51) Int. Cl.[7] ............................................. G01B 11/14
(52) U.S. Cl. ................................. 356/625; 250/559.25
(58) Field of Search ................................. 356/625, 602; 250/559.25; 382/106, 141, 154

(56) References Cited

U.S. PATENT DOCUMENTS

| | | |
|---|---|---|
| 3,976,384 A | 8/1976 | Matthews et al. |
| 4,188,544 A | 2/1980 | Chasson |
| 4,219,847 A | 8/1980 | Pinkney et al. |
| 4,394,683 A | 7/1983 | Liptay-Wagner et al. |
| 4,606,645 A | 8/1986 | Matthews et al. |
| 4,654,517 A * | 3/1987 | Reed ........................ 250/203.1 |
| 4,667,231 A | 5/1987 | Pryor |
| 4,891,772 A | 1/1990 | Case et al. |
| 4,916,629 A | 4/1990 | Bogue et al. |
| 4,937,445 A | 6/1990 | Leong et al. |
| 5,056,922 A | 10/1991 | Cielo et al. |
| 5,252,836 A | 10/1993 | Matthews et al. |
| 5,371,361 A * | 12/1994 | Arends et al. ............... 250/235 |
| 5,703,960 A | 12/1997 | Soest |
| 5,717,199 A | 2/1998 | Carbone et al. |
| 5,734,172 A | 3/1998 | Pryor et al. |
| 5,982,393 A | 11/1999 | Forchheimer et al. |
| 6,064,759 A * | 5/2000 | Buckley et al. ............. 382/154 |
| 6,252,974 B1 * | 6/2001 | Martens et al. ............. 382/107 |

* cited by examiner

Primary Examiner—Richard A. Rosenberger
Assistant Examiner—Vincent P. Barth
(74) Attorney, Agent, or Firm—Paul Smith Intellectual Property Law; Paul Smith (57) ABSTRACT

Disclosed herein are TV Camera based and other electro-optical sensors and systems, providing affordable methods and apparatus for high speed determination of dimensions and other features of objects. Particular embodiments capable of fast and reliable acquisition of features of moving objects such as boards and wood products are disclosed. Preferred embodiments utilize laser triangulation range detection with at least two cameras viewing the same laser spot or line projected on the object.

32 Claims, 7 Drawing Sheets

METHOD AND APPARATUS FOR SCANNING LUMBER AND OTHER OBJECTS

This application claims benefit of U.S. Provisional Application Ser. No. 60/227,015 filed Aug. 23, 2000 and Ser. No. 60/227,017 filed Aug. 23, 2000.

CROSS REFERENCES TO RELATED CO-PENDING APPLICATIONS

U.S. Ser. No. 60/227,015 "High Speed and Reliable Determination of Lumber Quality Using the Tracheid Effect", by Metcalfe and Dashner, filed the same day, the disclosure of which is incorporated herein by reference.

U.S. Ser. No. 09/931,179 "High Speed Camera Based Sensors", by Metcalfe and Reuser, filed the same day, the disclosure of which is incorporated herein by reference.

FIELD OF THE INVENTION

The invention relates to TV Camera based and other electro-optical sensors and systems, providing affordable methods and apparatus for high speed scanning of dimensions and other features of objects.

The invention uses one or more light sources combined with TV cameras whose output is used as input to a computer, such as a PC. This data is analyzed to typically provide data concerning the location or dimension of objects or parts of objects and/or the presence or characteristics of certain features of objects.

The invention is particularly useful for applications relating to wood products, including boards moving at high speed on conveyor lines in sawmills. More specifically it is concerned with triangulation sensors for object dimension, shape, thickness and position determination, especially at multiple locations on moving boards up to 28 feet long and at 3 boards per second. Data taken with such sensors is used to control sophisticated sawing operations aimed at maximizing yield from boards of variant shape, particularly in their edge regions.

A large number of data points per piece (e.g. every 0.1 inch or greater) is today considered essential to obtain a high quality 3D representation of the object shape so as to optimally control sawing operations used to maximize the yield of logs sawn. The invention discloses novel methods and apparatus to achieve this goal.

BACKGROUND OF THE INVENTION

Laser triangulation sensors have found favor in industry, particularly the lumber industry where, for example, requirements exist to determine shape, thickness or local contour of 28 foot long boards moving sideways on chain conveyors at 3 boards per second, in order to control the saws used to trim the boards of non conforming stock. Current trends call for more and more board sections to be taken, in order to better categorize the product and its subsequent sawing or other processing steps.

Over the last few years, sectional data density requirements have steadily progressed from one section every 6 inches of axial board length, to the existing state of the art of every one inch. This application seeks to improve this ability to every 0.1 inch or better down the length of a 16 foot board, say, while still maintaining the high quality of data with minimum latency needed to control actual process operations.

In the specific area of interest of this application in the field of wood measurement, examples of laser triangulation based sensor units specifically designed for this are Leong et al: U.S. Pat. No. 4,937,445, entitled Apparatus for determining the distances of points on a surface from a reference axis and Cielo et al, U.S. Pat. No. 5,056,922 entitled Method and apparatus for monitoring the surface profile of a moving workpiece. Both of these applications illustrate systems which represent the norm today for measuring moving boards, in which the direction of board motion is transverse to the longitudinal or long axis of the board. The lens axis, detector array and the longitudinal axis of the board are all basically in a common plane.

For the case of boards traveling in the direction of their longitudinal axis, a light stripe type system such as Chasson, U.S. Pat. No. 4,188,544 entitled Method and Apparatus for Automatically Processing a workpiece employing calibrated scanning, can be employed. Handling boards however, in this manner at high speed needed to cover all the board is very difficult.

A generic reference on dimensional and positional measurement of objects by Electro-optical means is Pryor et al: U.S. Pat No. 5,734,172 entitled Method and apparatus for electro optically determining the dimension, location and attitude of objects (the disclosure of which is incorporated by reference). Other references disclosing triangulation measurements with photo-detector arrays are; U.S. Pat. No. 4,891,772 Case et al. entitled Point and line range sensors; and Liptay-Wagner et al, U.S. Pat. No. 4,394,683 entitled New photodetector array based optical measurement systems. The use of first moment calculations to determine a image location is described in U.S. Pat. No. 4,219,847 by Pinkney et al. entitled Method and apparatus of determining the center of area or centroid of a geometrical area of an unspecified shape lying in a larger x-y scan field.

Further incorporated herein by reference is a provisional patent application entitled "High Speed Camera based Sensors", filed by our colleagues Leonard Metcalfe and Cash Reuser on the same day as this application.

Also incorporated by reference is an application by our co-worker, Richard McBain, entitled High speed laser Triangulation Measurements of Shape and Thickness, claiming benefit of U.S. Provisional application No. 60/135,680.

U.S. Pat. No. 5,717,199 by Carbone et al. discloses methods and apparatus by which data can be read randomly from pixels of a camera, while U.S. Pat. No. 5,982,393 by Forchheimer et al. describes methods by which computing can be done directly on pixel data using processors located on the same image chip. However, neither reference discloses methods by which such devices can actually be used to make practical measurements required in industry in an apparatus such as disclosed herein.

Categorization of lumber defects such as knots, is discussed in our copending application referenced above as well as U.S. Patents such as Mathews et al. U.S. Pat. No. 3,976,384 and Soest, U.S. Pat. No 5,703,960.

SUMMARY OF THE INVENTION

This invention relates to a significant advance over the state of the art as disclosed in Leong, Cielo et al. etc, and others for measuring boards moving transversely at the high speeds needed to provide information to real time sawing and other operations in lumber mills. One aspect covers a novel sensor arrangement, in which the camera system is oriented 90 degrees to that known heretofore, and uses novel signal processing methods to achieve the necessary data density, speed and obscuration elimination desired.

A preferred embodiment utilizes laser triangulation with a multiplicity of points, or one or more lines, said points or lines extending in the direction of the longitudinal axis of the object and perpendicular to the transfer direction of the object. Images of points on the surface of the object are determined in their position by two cameras one on each side of point or line projection direction, which as disclosed can eliminate problems with obscuration which otherwise would render inadequate a device such as that of Chasson if employed in this way.

The invention in some embodiments also utilizes a knowledge of the part itself to control the sensing characteristics to facilitate determination of object location or dimension in the presence of undesirable conditions caused by the surface condition of the object, which may be, for example, different surfaces of a moving board, or log, which face in the direction of motion or away from same.

It is noted that in the following discussion, the word "laser" is meant to connote not only the laser device itself of whatever kind (typically a semi-conducting diode laser), but also any associated optics and power sources needed to assure that reliable optical energy can be delivered to a zone on the surface of the object to be measured. Typically, but not necessarily, such a zone is produced by focusing the radiation emanating from the laser to a small zone at the mean point of object location in the laser projection direction. In other cases cylindrical optics are used to create line projections. Optics may be either refractive, reflective or diffractive/holographic in nature.

While the preferred detector array employed for board measurement to date has been a CCD, or charge coupled device, type array (for example a Reticon 1024C linear CCD type), this application is particularly concerned with use of specialized matrix array types, including, but not limited to CMOS as well as CCD types, capable of random or quasi-random scanning of their respective pixel outputs.

GOALS OF THE INVENTION

It is a goal of the invention to provide a triangulation device, employing at least one photo-detector array camera and projecting on an object multiple projected laser or other light zones, which overcomes reflection, obscuration and other problems caused by object surface shape and other discontinuities while operating at the highest possible operational speed, with acceptable accuracy and at reasonable cost.

It is a further goal of the invention to provide high density data via a novel sensory arrangement in which two camera devices are disposed in the direction transverse to the object longitudinal axis for viewing light zones projected along the object longitudinal axis and for discerning from comparison of data obtained from the cameras the range data corresponding to each zone, even in the presence of object occlusions, obscurations, or areas of unusual reflectance.

It is a goal of the invention to provide means to economically and accurately measure object length as well as obtain thickness and profile related information.

It is another goal of the invention to allow the reconstruction of object curved edges and other regions measured at high speed by using interpolated or extrapolated data, for example to fill in readings obtained.

It is also a goal of the invention to provide a method for increasing the reliability of detection of projected zones on objects with variant reflectance characteristics at different portions of their surface.

It is another goal of the invention to provide a method to control sensing characteristics with respect to moving objects using a knowledge of their movement and shape.

It is a still further goal of the invention to provide a triangulation device, employing a pair of twin PSD (position sensing diode) array based cameras in a novel arrangement in the direction of object motion utilizing a projection on an object of multiple projected laser or other light zones.

PREFERRED EMBODIMENTS OF THE INVENTION

Figure 1:
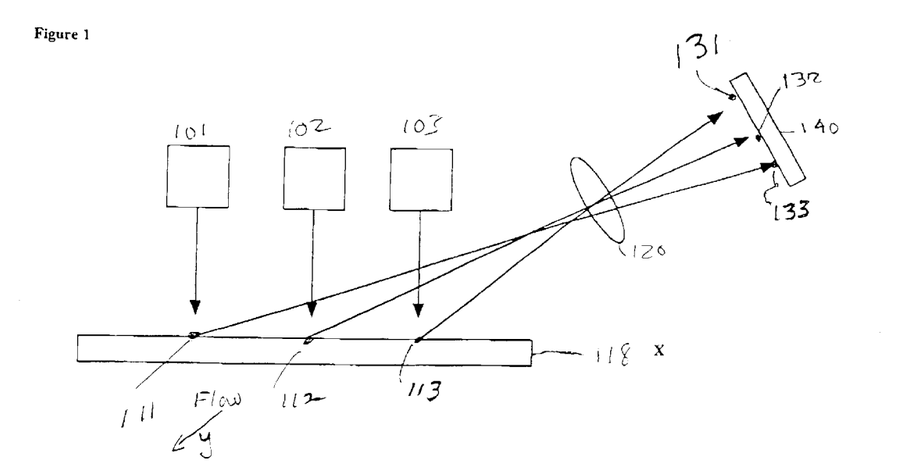
FIG. 1 illustrates an example of the prior art, typified by the Leong et al. and Cielo et al. patents.

FIG. 1

FIG. 1 illustrates a typical sensor, of the type disclosed in Leong et al. or Cielo et al. references mentioned above, used for generation of cross sectional data on boards moving transverse to their longitudinal axis (x axis in the drawing of FIG. 1). For simplicity only 3 lasers are here shown, projecting 3 zones on a moving board. However sensors in the trade today have up to 24 lasers in such an arrangement.

The lasers 101–103 typically project substantially round or elongate zones 111–113 on the board 118, which are imaged by lens 120, to form images 131–133 on a detector array 140 typically, a linear array such as a Reticon 1024C. This arrangement has proven very valuable in practice as it allows measurement of the board and the edges thereof without obscuration, and at high speed. The board is moving out of the plane of the drawing at typically >3 feet per second.

However, as the density of points in the longitudinal direction "x" of the board increases, this arrangement becomes increasingly cumbersome. The state of the art today achieves points on 1 inch centers in the x direction, but has considerable difficulty when variant wood is observed, and some aspects and difficulties of such measurements are discussed in the McBain application incorporated herein by reference.

It is thus desirable to have a sensor which can cover a much larger number of data points in the longitudinal direction (that is achieve a higher point density in the x direction), but at the same time operate at high measurement speeds needed to resolve the same density of points in the "y" direction of motion—particularly in the region of the edges of the board where most definition is needed for sawing operations, and at the same time avoid obscuration and other effects.

Figure 2A:
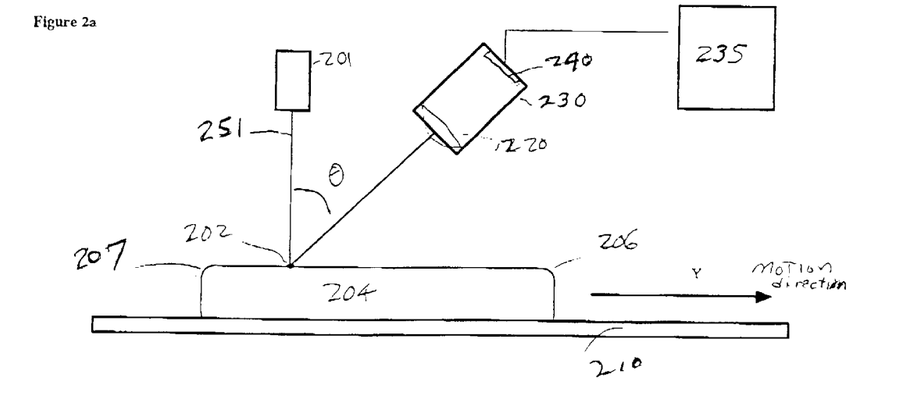
FIGS. 2a–c illustrate an obscuration problem with moving contoured objects, when the camera system is oriented in the plane of the direction of object motion.
Figure 2B:
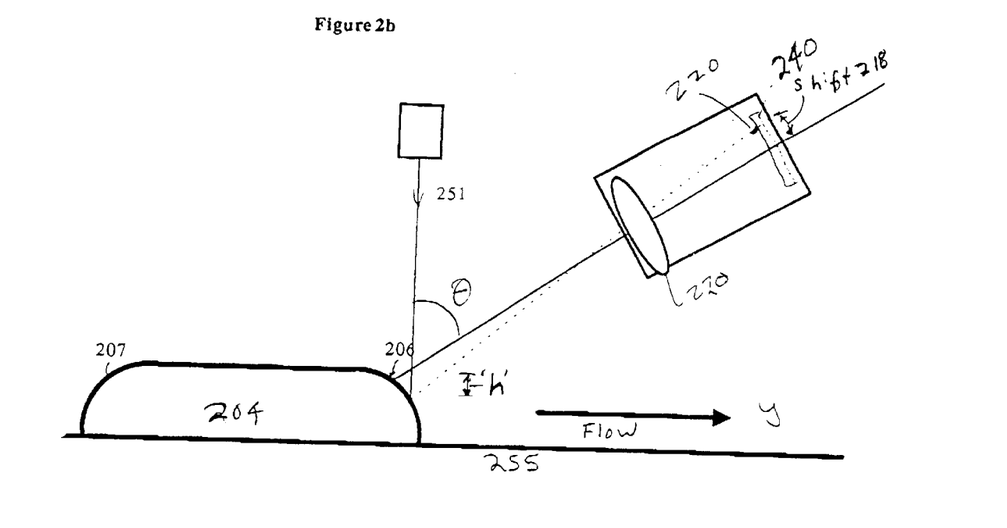
Figure 2C:
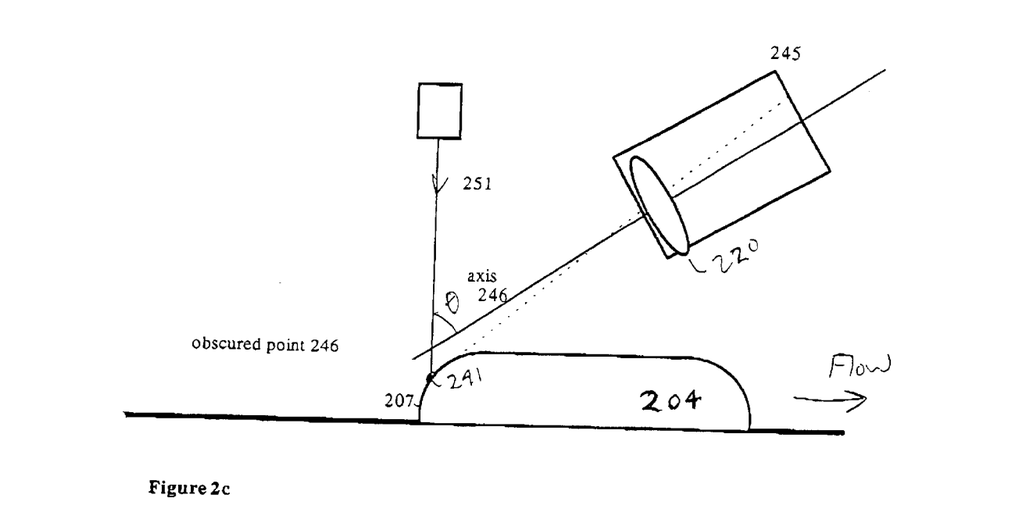

FIG. 2

At this point it is of interest to illustrate triangulation measurement and the obscuration problem which occurs if one views the board from another vantage point than that of FIG. 1 above, where the viewing direction is oriented longitudinally.

FIG. 2 illustrates obscuration and other problems with moving contoured objects. As shown in FIG. 2a, a laser 201 projects a zone of light 202 onto the object 204, in this case a moving board having a shaped edges 206 and 207, being transported on a conveyor 210.

As disclosed in the references, triangulation measurements of board location and shape can be made using a lens such 220 to image the zone on to a photo-detector 230 which is processed by means 235 to give an output indicative of the position of the zone image 240 on the photo-detector. This arrangement is particularly of use in profiling the shape or thickness of objects in multiple sections (spaced out of the plane of the drawing), such as is desirable for determining parameters of ostensibly flat boards in sawing operations in lumber mills.

Typically such sensors employ photo-detectors which are photo-detector arrays of either linear or matrix types, or Position sensing photodiodes (PSDs) which provide image position data as a voltage. Where photo-detector arrays are used, processing to determine zone image position can be using thresholded centroids and multiple centroids as described Pryor et al, derivatives as described in Liptay-Wagner et al, U.S. Pat. No. 4,394,683 entitled New photo-detector array based optical measurement systems, or first moment calculations as described in U.S. Pat. No. 4,219,847 by Pinkney et al. entitled Method and apparatus of determining the center of area or centroid of a geometrical area of unspecified shape lying in a larger x-y scan field, or by any other suitable means.

FIG. 2b illustrates the case when the curved edge 206 of board 204 is measured, as it passes under the laser beam 251 due to the motion of conveyor 255. The distance "h" of movement in the z or range direction, of the projected spot from the laser beam hitting the board causes a shift 218 of spot image position 219 formed by lens 220 on the detector array 240, for example a Reticon 1024C. Alternatively another spot image position sensing device such as a Position Sensing Diode, or "PSD" such as those made by SiTek Company of Sweden.

FIG. 2c illustrates the case of edge 207 on the opposite side of board 204 as it passes under the sensor unit shown due to conveyor motion. As can be seen, at a certain location on the edge profile, data points such as 241 on board edge 207 cannot be seen by the camera 245 as the camera axis 246 is of necessity at an angle theta to the direction of projected light incidence 251 in order to determine range by triangulation (which range answer can be used to compute the dimension, shape, thickness or other variable of the board). When used for such board measurement, the triangulation angle theta and lens system magnification, is typically chosen such that the unit has a range of approximately 8 inches in the vertical or z direction, for any given choice of detector array size in the array y direction. Resolution then depends on the density of pixels in the array and the degree of sub-pixel precision obtainable in determining zone image location.

If theta is made to small, to avoid as much obscuration as possible, the accuracy of the sensor system can be rendered inadequate for the job. Thus in practical terms, with many boards, and many sensor units, the obscuration of the sort depicted can occur.

In addition to this problem, it should be noted that sometimes severe lighting problems can occur, due to the reflection of the incident light from the part, both due to the angle with respect to the camera, and the sometimes discolored nature of the object surface.

Figure 3:
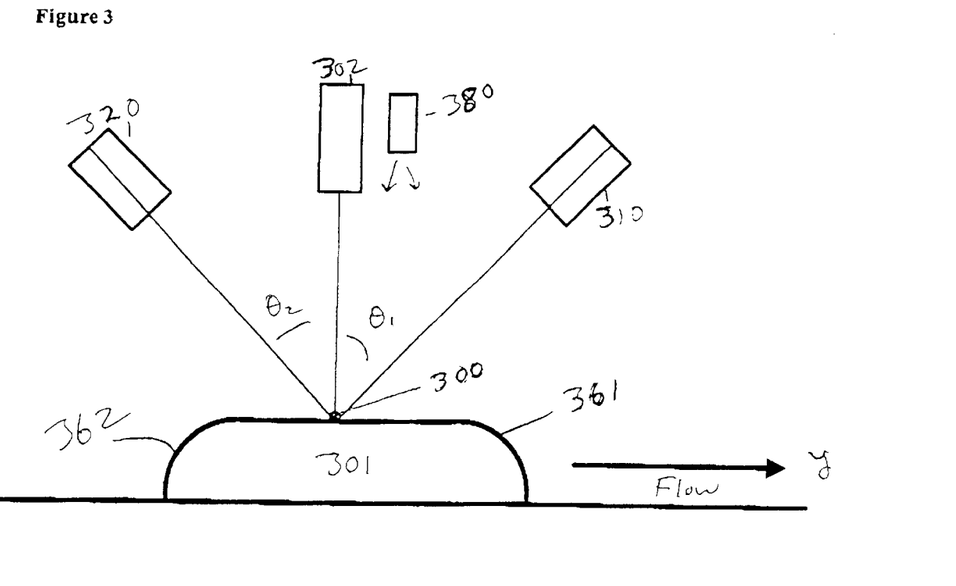
FIG. 3 is a simplified side view of a preferred two camera embodiment of the invention used for measuring moving boards in a sawmill, and further incorporating means to control sensor characteristics such as light power, exposure or data density from board shape or location.

FIG. 3

FIG. 3 is a simplified, partly diagrammatic side view of a preferred two camera embodiment of the invention, in which a single projected laser zone 300 is directed at the object 301 by laser 302 and viewed by two cameras, 310 and 320, angularly spaced (typically by the same angle, but not necessarily so) in the direction of motion of the object on opposite sides of the laser projection axis.

Use of this two camera arrangement, allows at least camera to obtain an unobstructed view of the laser zone no matter which edge is present. And where obstruction doesn't occur, both cameras can be used to view the zone, adding to the resolution and redundancy of the system. This is also useful when a depression in the board is present, such as a knot, which can also cause one view or the other to be obstructed.

A control algorithm allows one to take the average value of the position signal, as long as both fall with in certain parameters of image quality. When one signal is not of such quality, the other is used, or a weighted average is employed.

Another control algorithm usable by the invention, allows the laser power, camera integration, or other parameter to be controlled by a knowledge of the position and shape of the object. For example as the object comes into view, it is clear that edge 361 will first be viewed, given the direction of object motion. This means that camera 310 will be used exclusively for this measurement, and that laser power from laser 302 will start at a high value indicated of the steep slope and often poor surface condition expected (both causing less light to reach the camera). By running the laser power (or other control of delivered energy per unit time such as pulse time or frequency) at near maximum levels (for a range of object information expected), one can in turn maximize the speed of response of the camera, for example by using higher scan rates. Such speed of response is desirable for maximum data density and or production throughput.

For a dual camera unit as shown, laser power delivered into the zone affects the choice of detector variables for both cameras. When higher power is needed for the one camera on an extreme edge of the object, the other camera exposure variable such as scan rate or integration time is altered to keep it with in the dynamic range desired.

In the middle of the board, between edges 361 and 362, less data is needed, as an object such as a sawn board hardly varies in shape in this area. In this case data may be taken relatively infrequently. This allows data interface to keep transferring data from the edge zone, even while the slower rate of change data is being acquired.

Figure 6:
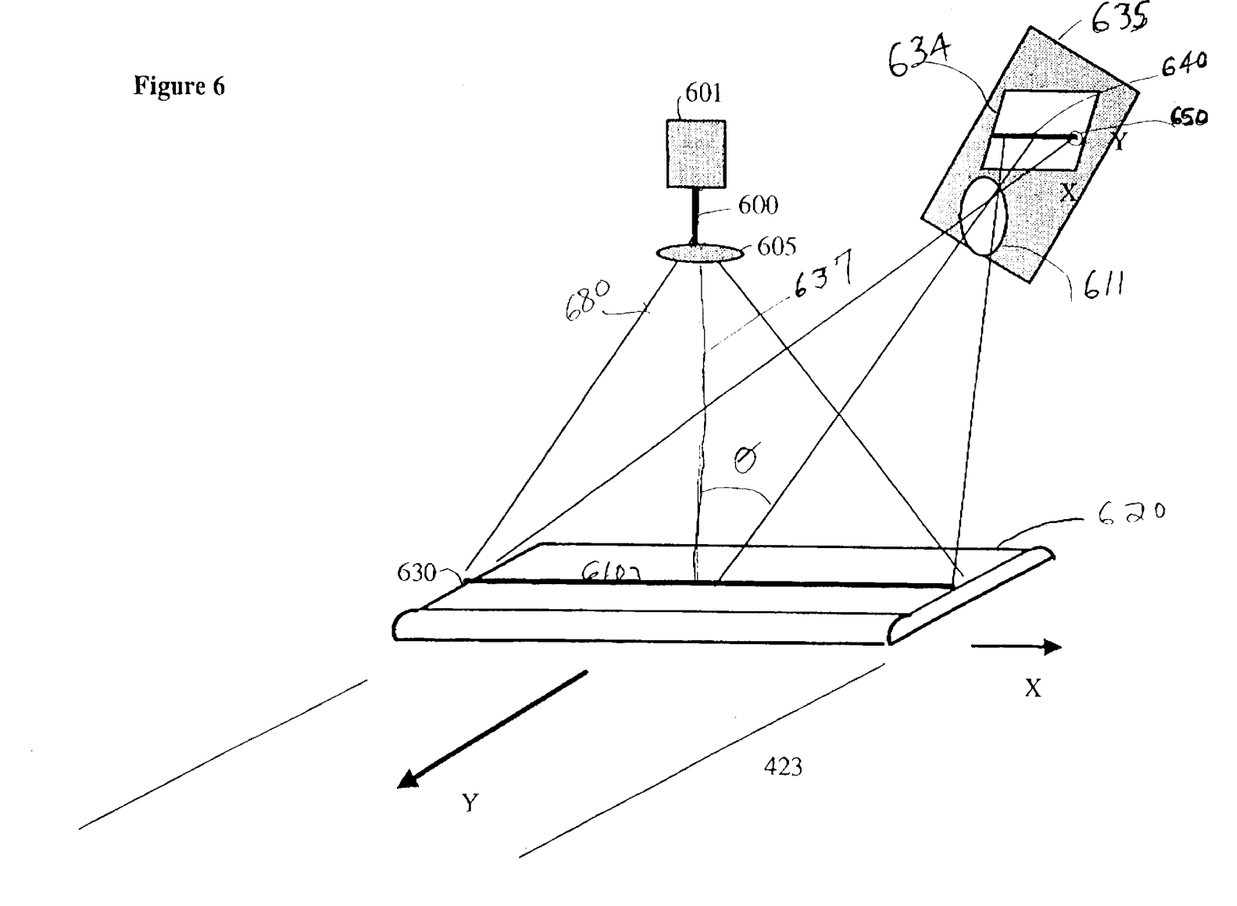
FIG. 6 illustrates an embodiment of the invention similar to FIG. 4, employing a line laser source and a single array.

Another issue concerns multiple zones, such as FIG. 4 below or line type zones such as depicted in FIG. 6 below, where all zones, or a continuum of zones forming a line are viewed by the same array. In this case laser power in each zone can be changed, to suit light requirements of image scanning, but the array integration time and scan rate is fixed the same for all zones—if standard matrix array cameras (e.g. CCD TV type) are used. However with pixel addressing types this situation can be improved, as disclosed in the referenced co-pending application, "High Speed Camera based Sensors". Use of such is preferable, we have found.

It is noted that optionally such as system can be advantageously combined with sensor such as 380 as described in our co-pending referenced application for a lumber grain related defect detection device. Typically such as sensor would view the board substantially along a normal to the board as shown, though this is not necessary in all cases.
FIG. 4

Figure 4:
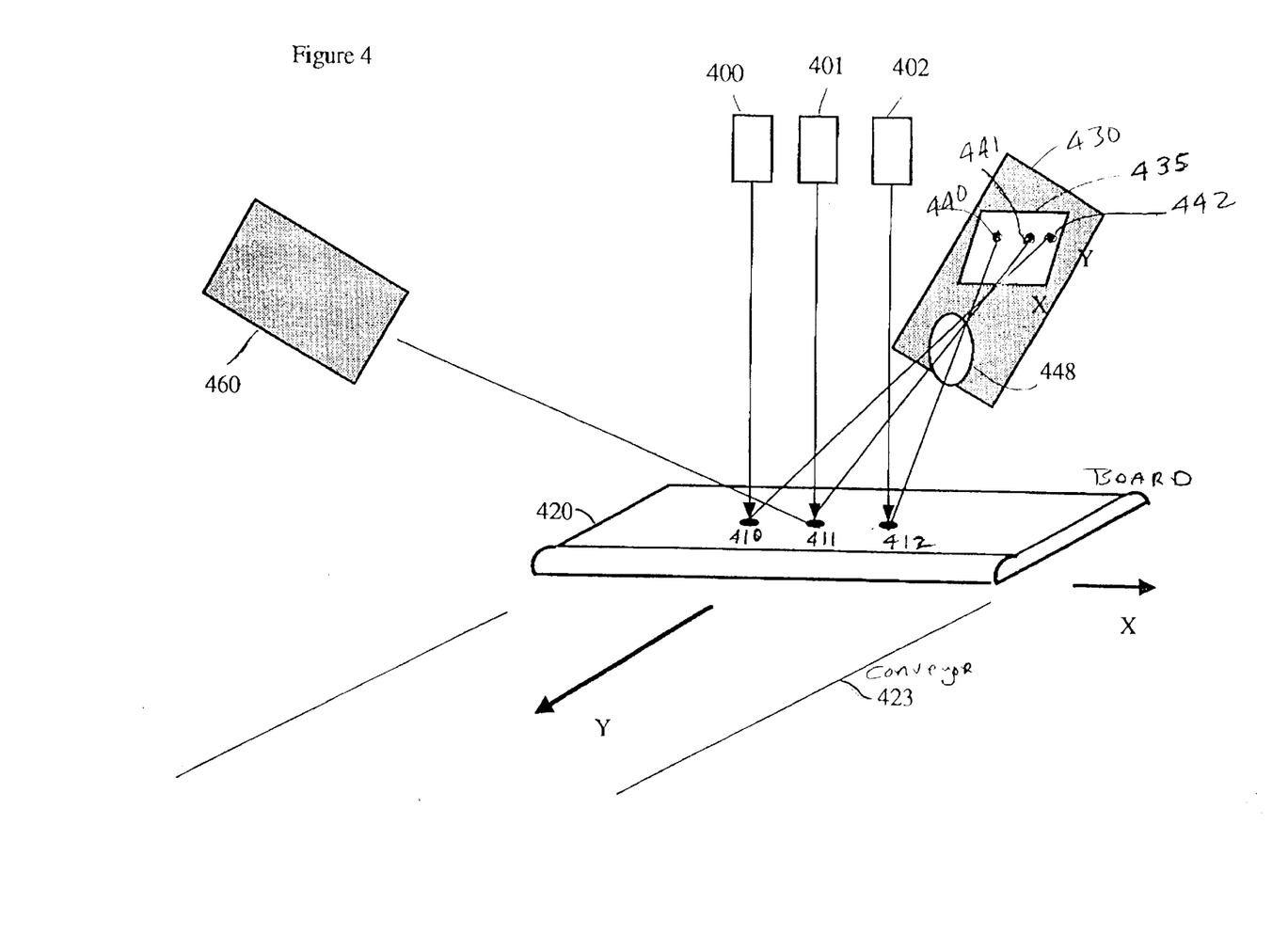
FIG. 4 illustrates an embodiment of the invention similar to FIG. 3, employing multiple laser sources and a single array.

FIG. 4 illustrates an embodiment of the invention similar to FIG. 3, employing multiple laser sources disposed in the transverse direction to that of a moving object such as a board, and a single matrix photo-detector array. As shown 3 independent laser sources 400, 401 and 402 direct zones of light, 410–412, in this case spot shaped, at a board 420 as shown, traveling on a chain conveyor 423 in the Y direction at 30 inches/second. The zones are in a line, parallel to the long axis (x axis) of the board, and perpendicular to the conveyor flow.

A camera 430, composed of photo-detector matrix array 435 and lens 448 is used to scan the images 440–442 of the projected laser spot zones 410–412 on the array. Each zone is analyzed for its position on the array as described below and for example in U.S. Pat. No. 5,734,172, thus providing location data of the board with respect to the sensor composed of the laser/camera combination. By taking sequential scans, a complete profile section for the board at each axial zone x location, can be built up during the rapid traverse of the board past the sensor station.

As disclosed in FIG. 3, a second camera such as 460 is often desirable to avoid obscuration and provide enhanced results.

Figure 5:
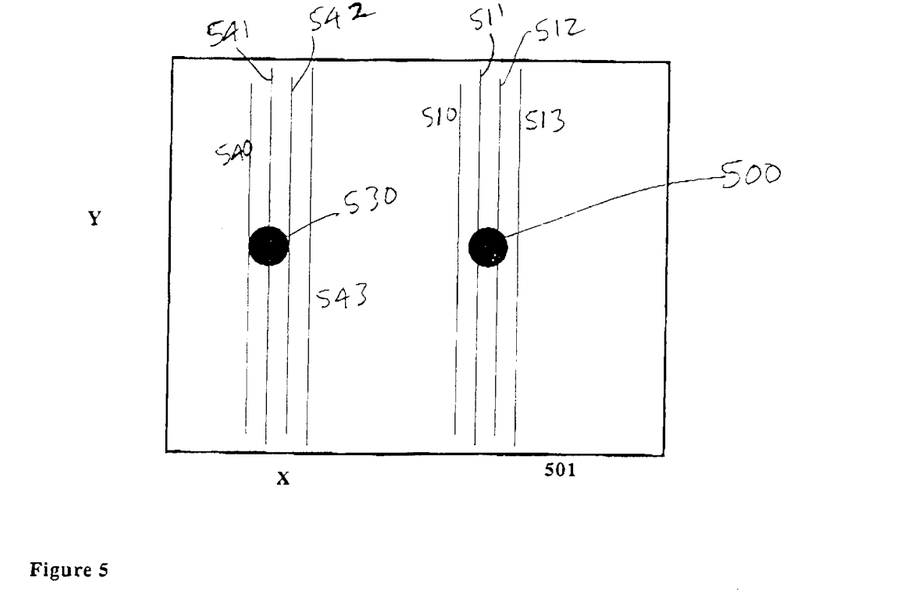
FIG. 5 illustrates a pixel scan and processing embodiment useful with the photo-detector array versions of the invention.

Alternative to the above, and even faster is to address individual pixels which need be scanned, while ignoring those pixels in the camera field which carry little or no relevant information. This is very desirable in the instant application and is described further in the application High Speed Camera based Sensors incorporated by reference herein.
FIG. 5

FIG. 5 illustrates a pixel scan and processing embodiment useful with the photo-detector array versions of the invention. For example, consider image 500 of a spot type projected zone which is detected by photo-detector matrix array 501 which is of a random line addressable or even random pixel addressable type, for example a Photon Vision Systems (Homer, N.Y.) ACS-I active column imager.

In the first mode of operation, scan lines of the array are chosen specifically to correspond to the expected location in the x direction across the array corresponding to the axis of the board perpendicular to the direction of motion (and out of the plane of the paper in the sectional drawings above).

To detect the one zone image, one just has to scan a few lines such as the four lines 510–513 of the array, in order to characterize the location of the zone in the y direction of the array (the direction of change of zone position with change in board dimension). One can determine the centroid of the zone portion 500 seen on the scan lines, and if desired, average the results to substantially improve resolution and eliminate errors due to surface condition, as taught in U.S. Pat. No. 4,667,231.

More zones than one can also be detected this way, and their position determined, using a single array. For example zone image 530 can be scanned by lines 540–543. The choice of which lines depends on the zone image location, and thence on the projected zone spacing on the object. Choosing to scan only where zone image information lies, results in a speed advantage, in direct proportion to the number of lines of the array divided by the number only needed to be scanned. In this instant example of two zone images, with 4 lines each needed or desired to find and characterize same, this means that a 800 line array operating at 30 scans per second, which only needed to scan 8 lines, would be able to run 3000 scans per second. This is very useful for high speed measurements. Perhaps more optimal would be 6 zone images per array, and 1000 scans per second.

Finally it is noted that when the invention is used with wood or other materials having similar grain, that as an option, each of the zones projected can also be looked at for elongation of one or more zone image axes and rotation thereof by the tracheid effect in order to determine the possible presence of defects such as knots, as described in our co-pending referenced application entitled: "High Speed and Reliable Determination of Lumber Quality Using the Tracheid Effect" incorporated by reference herein.
FIG. 6

FIG. 6 illustrates an embodiment of the invention similar to FIG. 4, employing however, a line laser source and a single photodetector array. As shown laser beam 600 from laser 601 is expanded by cylindrical optical element 605 (refractive, reflective or diffractive, as desired) to form a line 610 disposed longitudinally in the x axis down the long axis of a board, 620 moving transversely in y. In the particular case shown the line, or "fan" of points 680 extends past one edge of the board 630 whose position can be found as now described.

A matrix array 634 of camera 635 whose axis is oriented at an angle theta to the projection axis 637, of laser radiation can be used to sense the image 640 formed by lens 611 of line 610 on the board. As shown in the image, a contour of the board in the longitudinal direction is produced by the light section principle, and the location of the end 630 (which is typically sawed off) can be determined by the location of rapid contour fall of 650 in the image. By sequentially scanning lines of the array, the first location at which the line location is for example, 100 pixels less than the previous, can be chosen as the true end (not with standing a correction factor for parallax given the fan angles involved).

Such a system is capable of generating a large number of points along the line very quickly—the number equal if desired to the number of pixel lines in the array in the x direction, assuming the data as to line centroid location at a given x location on the board can be achieved rapidly. This can be preferably achieved though apriori knowledge of line location, as disclosed in the High Speed Camera based Sensors application incorporated by reference and disclosing the processing of data using pixel addressable cameras to determine the location of individual points on the projected line.

As shown in FIGS. 3 and 4, a dual camera system can be advantageously employed in this line zone example as well, to deal with obscurations and light level problems due to curved board edges in the y, or motion, direction. The line sensor having only one line source, has to control this power to give the best performance at all the sections of interest. This can be varied on a sectional basis by choosing which lines are used to set the power.
FIG. 7

Figure 7:
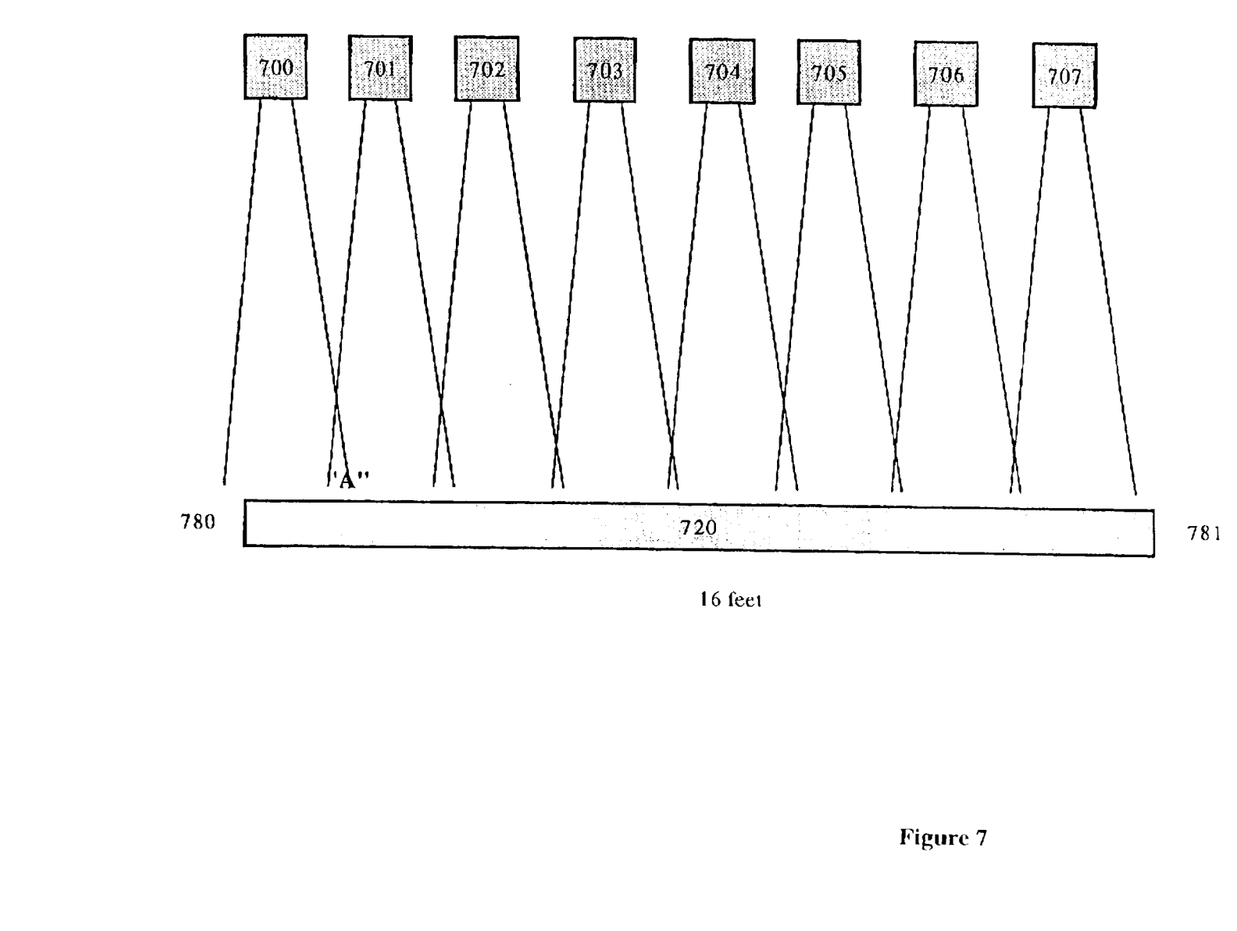
FIG. 7 illustrates an embodiment of the invention having multiple sensor heads and further illustrating a length measurement capability.

FIG. 6 illustrates an embodiment of the invention having multiple sensor heads, which can be of the multiple zone, or line continuum zone type as described above.

We have found in practicing the invention that a preferable arrangement is often to have a sensor which can see line or point zones over an approximate 24 inch length in the x direction of the board or other object, and then to have sensors, such as 700–707 of the FIG. 6 type, for example, butted end to end whose 24 inch sections slightly overlapped, for example in overlap region "A". Typical would be 16 foot board 720, axially irradiated and viewed by 8 sensors top, 8 sensors bottom (not shown for clarity) having two foot swaths each, to allow determination of thickness and bow. Note that boards however, can range 10 to 28 feet in length in lines used in North America).

Also as pointed out in FIG. 6, the sensor can also see the end of the board. Thus by using data from the sensors such as 700 and 707 covering the board ends, 780 and 781, and combining end location data obtained in a differential manner, this arrangement can provide a length measurement for the board.

Figure 8:
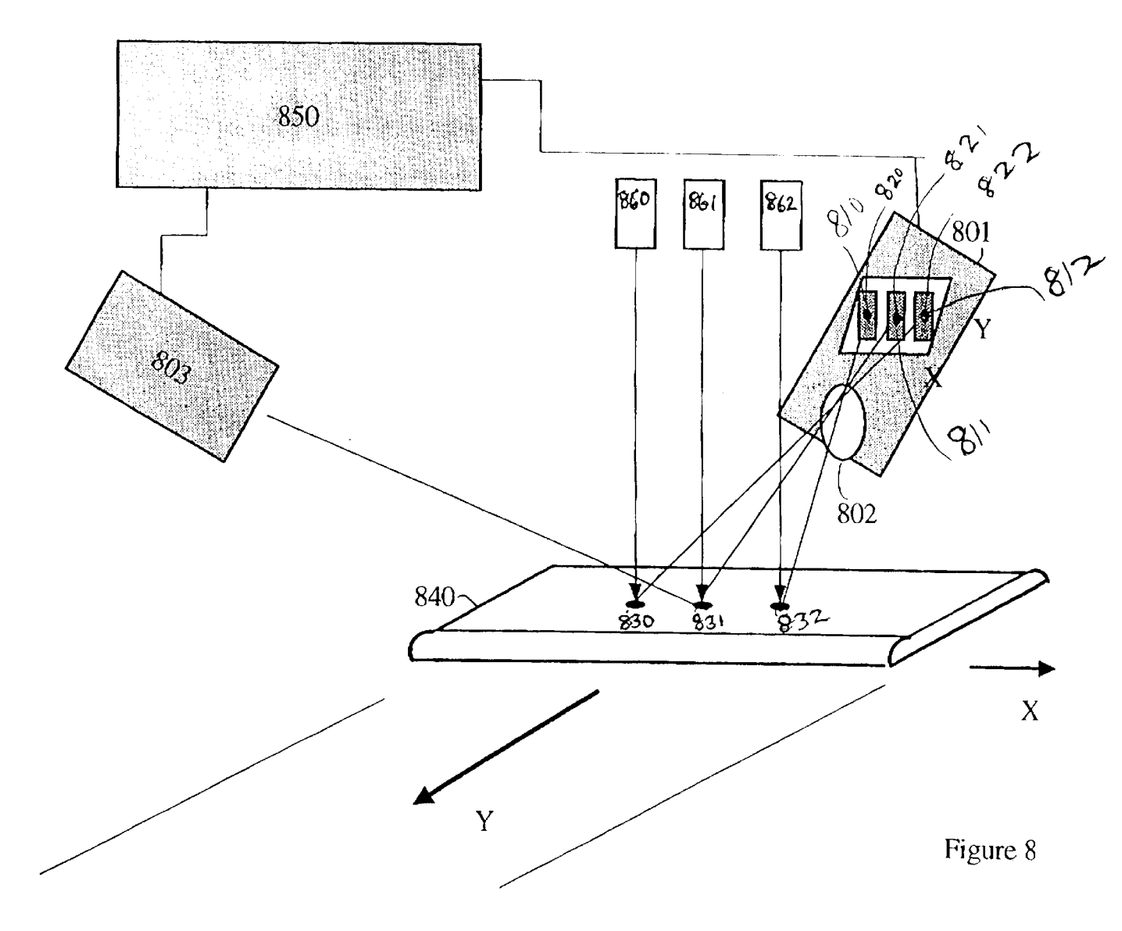
FIG. 8 illustrates a variation on the embodiment of FIG. 4 in which a PSD array is used.

FIG. 8

FIG. 8 illustrates a different type of camera 801 comprising lens 802 and a group of PSD (position sensitive diode) detectors 810–812 which detect zone images 820–822 of zones 830–832 projected on board 840 by lasers 860–862. Readout 850 analyzes the analog outputs of the PSD detectors to determine data concerning zone image location and thence board location with respect to the sensor.

As disclosed above, two cameras of this type, 801 and 803 can be used in a device such as that of FIG. 4 to provide obscuration free measurement at high speeds for example.

While only three such PSD detectors 810–812 are shown, it is possible to have an array of same, for example 128 in a row on a single substrate such as the in 3D device recently announced (see www.in3D.nl). This is capable of extremely high rates as each PSD detector on the array of detectors directly provides the answer as to the y location of the zone image on that position of the array, and the corresponding object location.

Use of such PSD arrays is described further in the application High Speed Camera based Sensors incorporated by reference herein.

What is claimed is:

1. A method for determining the dimension of an object moving on a conveyor, comprising the steps of:
   providing a first triangulation based sensor unit, including a light source projecting a zone of light on the surface of said object and a TV camera, said first sensor unit oriented substantially such that a plane including the light source projection axis and the camera axis of said first sensor unit is in the direction of conveyor motion;
   providing a second triangulation based sensor unit, including a light source projecting a zone of light on the surface of said object and a TV camera, said second sensor unit oriented substantially such that a plane including the light source projection axis and the camera axis of said second sensor unit is in the direction of conveyor motion;
   positioning said sensor units so that said first sensor unit views the object moving toward it due to the conveyor motion, while the second sensor unit views the object moving away from it;
   without using a geometric model of said object, analyzing the outputs of said sensor units; and
   from said analysis determining at least one dimension of said object.

2. A method according to claim 1 wherein said sensors have a common light source whose projection on the object is imaged by each camera.

3. A method according to claim 1 wherein said object is a board with curved edges transversely oriented with respect to the motion of said conveyor.

4. A method according to claim 1 wherein a single zone is projected by the light source of each sensor.

5. A method according to claim 1 comprising the further step of rejecting one of said sensor outputs if data relating to same is unreliable, due to obscuration, color, edge effects, piece alignment or illumination level.

6. A method according to claim 1 comprising the further step of averaging said sensor outputs.

7. A method according to claim 2 comprising the further step of controlling said light source to favor the sensor which has the best chance to obtain reliable data.

8. A method according to claim 7 wherein said control is based on knowledge of the object and its motion.

9. A method according to claim 1 wherein a plurality of zones spaced in the axial direction of the object are projected by the light source of each sensor.

10. A method according to claim 1 wherein said projected zone is a spot.

11. A method according to claim 1 wherein said projected zone is a line, substantially extending in the axial direction of said object and transverse to the direction of conveyor motion.

12. A method according to claim 11 wherein the length of said object is determined.

13. A method according to claim 9 wherein at least one of said sensors employs a PSD array.

14. A method according to claim 1 wherein said TV camera employs a photodetector array.

15. A method according to claim 14 wherein said array is pixel addressable such that only a portion of the pixels of said array need be interrogated to determine the desired object information.

16. A method according to claim 1 wherein said light source is a laser.

17. A method according to claim 1 wherein said light source is controlled to allow operation over a wide range of object reflectivity conditions.

18. A method according to claim 1 wherein a parameter of said TV camera is controlled to allow operation over a wide range of object reflectivity conditions.

19. A method according to claim 1 wherein said light source and said TV camera are controlled to allow operation over a wide range of object reflectivity conditions.

20. A method according to claim 3 wherein said light source is projected perpendicular to the axis of conveyor motion.

21. A method according to claim 1 wherein the shape of an edge of the board is measured.

22. A method according to claim 1 wherein data on curved edges is reconstructed by interpolation or extrapolation of other data taken.

23. An improvement in measuring boards on a conveyor using optical triangulation sensors, comprising the steps of:
   projecting a zone of light on said board;
   without using a geometric model of said board, predicting data relating to the likely location of the board surface, and therefore the image of the zone on the board; and
   imaging said zone with a TV camera having a photodetector array which can be addressed such that the pixels of the array which are interrogated are those in the vicinity of the expected location of the image of the zone, given said predicted board surface location.

24. A method according to claim 23 wherein said projected zone is a spot.

25. A method according to claim 23 wherein a plurality of said zones are projected and imaged by said TV camera.

26. A method according to claim 23 wherein said projected zone is a line.

27. A method according to claim 23 wherein said light is projected by a laser.

28. A method according to claim 23, wherein said predicted location is substantially near where the previous detected location was.

29. A method according to claim 23, wherein said predicted location is substantially near where one would assume given the nominal dimensions of the board.

30. A method according to claim 23, wherein said predicted location is substantially near where one would assume given the dimensions of a previously measured board.

31. A method according to claim 23 wherein the shape of an edge of the board is measured.

32. A method according to claim 23 wherein data on curved edges is reconstructed by interpolation or extrapolation of other data taken.

* * * * *